(12) United States Patent
Yoo et al.

(10) Patent No.: US 11,109,760 B2
(45) Date of Patent: Sep. 7, 2021

(54) IMAGING CATHETER SYSTEM

(71) Applicants: INDUSTRY-UNIVERSITY COOPERATION FOUNDATION HANYANG UNIVERSITY, Seoul (KR); KOREA UNIVERSITY RESEARCH AND BUSINESS FOUNDATION, Seoul (KR); KOREA ADVANCED INSTITUTE OF SCIENCE AND TECHNOLOGY, Daejeon (KR)

(72) Inventors: Hong Ki Yoo, Seoul (KR); Min Woo Lee, Suwon-si (KR); Hyeong Soo Nam, Seoul (KR); Wang Yuhl Oh, Daejeon (KR); Jin Won Kim, Seoul (KR); Woo Jae Kang, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 502 days.

(21) Appl. No.: 15/963,502

(22) Filed: Apr. 26, 2018

(65) Prior Publication Data

US 2018/0310826 A1 Nov. 1, 2018

(30) Foreign Application Priority Data

Apr. 28, 2017 (KR) ........................ 10-2017-0055129

(51) Int. Cl.
*A61B 5/00* (2006.01)
*A61B 90/00* (2016.01)
*A61B 1/00* (2006.01)

(52) U.S. Cl.
CPC ........ *A61B 5/0066* (2013.01); *A61B 1/00009* (2013.01); *A61B 5/0071* (2013.01);
(Continued)

(58) Field of Classification Search
CPC ... A61B 5/0066; A61B 5/0084; A61B 5/0071; A61B 5/0086; A61B 2562/0233; A61B 2090/3735; A61B 1/00163; A61B 1/07
See application file for complete search history.

(56) References Cited

U.S. PATENT DOCUMENTS

2005/0165303 A1   7/2005   Kleen et al.

FOREIGN PATENT DOCUMENTS

| JP | 2000-252559 A | 9/2000 |
|---|---|---|
| JP | 2000-304697 A | 11/2000 |

(Continued)

OTHER PUBLICATIONS

Lee et al. 2014 Circulation Cardiovascular Interventions 7:560-569 and online supplement (Year: 2014).*

(Continued)

*Primary Examiner* — Michael J Tsai
*Assistant Examiner* — Patrick M Mehl (57) ABSTRACT

Disclosed is an imaging catheter system that utilizes optical coherence tomography and autofluorescence lifetime imaging microscopy. The disclosed imaging catheter system may include: an autofluorescence light source; an OCT device; a catheter device configured to receive rays inputted from the autofluorescence light source and an OCT light source of the OCT device and scan a specimen; an optical detector unit configured to detect autofluorescence generated from the specimen; and a first optics system configured to transfer the autofluorescence to the optical detector unit and transfer a ray of the OCT light source reflected from the specimen to the OCT device.

11 Claims, 4 Drawing Sheets

(52) U.S. Cl.
CPC .......... *A61B 5/0073* (2013.01); *A61B 5/0084* (2013.01); *A61B 5/0086* (2013.01); *A61B 90/36* (2016.02); *A61B 5/7271* (2013.01); *A61B 2090/3735* (2016.02); *A61B 2562/0233* (2013.01)

(56) References Cited

FOREIGN PATENT DOCUMENTS

| | | | |
|---|---|---|---|
| JP | 2002-095624 | A | 4/2002 |
| JP | 2008-506426 | A | 3/2008 |
| JP | 2008-171985 | A | 7/2008 |
| KR | 10-2014-0011095 | A | 1/2014 |
| KR | 10-1352960 | B1 | 1/2014 |
| KR | 10-1397272 | B1 | 5/2014 |
| KR | 10-2016-0133351 | A | 11/2016 |

OTHER PUBLICATIONS

Ughi et al. 2016 JACC Cardiovasc. Imaging 9:1304-1314; combined with online supplement (Year: 2016).*

Park et al. 2010 Biomed. Optics Express 1:186-200 (Year: 2010).*

Keiser 2016 reference textbook Biophotonics: Concepts to Application—Graduate Texts in Physics, Edt G. Keiser, Springer 2016 (Year: 2016).*

Pahlevaninezhad et al. 2014 Biomed Optics Express 5:2978-2987 (Year: 2014).*

Wang 2014 Ph.D. Thesis Boston University College of Engineering, 251 pages (Year: 2014).*

Min Woo Lee, Woo Jae Kang, Hyeong Soo Nam, Joon Woo Song, Jin Won Kim, Wang-Yuhl Oh, Hongki Yoo, "Intravascular Optical Coherence Tomography and Fluorescence Lifetime Imaging Catheter for Diagnosing Coronary Artery Disease (CAD)", Nano-Bio Sensing, Imaging & Spectroscopy 2017.

Jesung Park, Javier A. Jo, Sebina Shrestha, Paritosh Pande, Qiujie Wan, and Brian E. Applegate, A dual-modality optical coherence tomography and fluorescence lifetime imaging microscopy system for simultaneous morphological and biochemical tissue characterization, Biomed Opt Express. Aug. 2, 2010; 1(1): 186-200.

* cited by examiner

IMAGING CATHETER SYSTEM

CROSS-REFERENCE TO RELATED APPLICATIONS

This application claims the benefit of Korean Patent Application No. 10-2017-0055129, filed with the Korean Intellectual Property Office on Apr. 28, 2017, the disclosure of which is incorporated herein by reference in its entirety.

BACKGROUND

1. Technical Field

The present invention relates to an imaging catheter system, more particularly to an imaging catheter system that uses optical coherence tomography and autofluorescence lifetime imaging microscopy.

2. Description of the Related Art

The imaging catheter, used in diagnosing cardiovascular diseases, etc., is being utilized in the field of clinical medicine, where the related art includes methods based on ultrasonic technology, near-infrared imaging technology, optical coherence tomography technology, etc.

Methods based on ultrasonic technology may entail inserting a device in the form of a catheter into a specimen such as a blood vessel, etc., to obtain tomographic images, and these methods are as yet the most often utilized in hospitals for obtaining intravascular images. Since these methods use ultrasonic technology, the resolution is relatively low, at levels of about 100 µm, the contrast is also low, and the speed of acquiring the images is slow, taking about 30 seconds.

Methods based on near-infrared imaging technology may entail detecting the presence of lipids on the inner walls of blood vessels by using near-infrared rays for spectrometry. Recent developments have also provided products that combine near-infrared imaging technology and ultrasonic technology into a single catheter.

Methods based on optical coherence tomography technology may entail inserting a device in the form of a catheter in a manner similar to that of using ultrasonic technology, emitting rays into a blood vessel, and acquiring tomographic images of the blood vessel by analyzing the rays that return. The principles of a white light interferometer and a confocal microscope are collectively utilized to obtain the ultrastructure within a biological tissue.

Also, there are imaging catheter systems being implemented that combine optical coherence tomography technology with near-infrared fluorescence imaging or near-infrared spectroscopy.

SUMMARY OF THE INVENTION

An aspect of the invention is to provide an imaging catheter system by using optical coherence tomography and autofluorescence lifetime imaging microscopy.

Also, an aspect of the invention is to provide an imaging catheter system that can prevent reductions in the coupling efficiency of the rays and can decrease the effect of autofluorescence acting as an artifact.

To achieve the objectives above, an embodiment of the invention provides an imaging catheter system that includes: an autofluorescence light source; an OCT device; a catheter device configured to receive rays inputted from the autofluorescence light source and an OCT light source of the OCT device and scan a specimen; an optical detector unit configured to detect autofluorescence generated from the specimen; and a first optics system configured to transfer the autofluorescence to the optical detector unit and transfer a ray of the OCT light source reflected from the specimen to the OCT device.

Also, to achieve the objectives above, another embodiment of the invention provides an imaging catheter system that includes: an autofluorescence light source; a catheter device configured to receive rays inputted from the autofluorescence light source and scan a specimen; an optical detector unit configured to detect autofluorescence generated from the specimen; and a collimator configured to receive input of rays from the autofluorescence light source to transfer the rays to the catheter device via a double-clad fiber and also transfer the autofluorescence to the optical detector unit, where a first time at which the autofluorescence generated from the specimen is detected at the optical detector unit is later by a threshold time or more than a second time at which the autofluorescence generated by a core of the double-clad fiber of the collimator is detected at the optical detector unit.

By using the autofluorescence generated from a tissue, an embodiment of the invention does not require an external contrast agent and can therefore provide advantages in terms of obtaining clinical approval compared to using near-infrared imaging technology. Moreover, the autofluorescence generated from various biochemical components of the tissue can be imaged concurrently.

Also, an embodiment of the invention can prevent reductions in the coupling efficiency of the rays and can decrease the effect of autofluorescence acting as an artifact.

As an embodiment of the invention can detect the autofluorescence generated from various components of the tissue with the autofluorescence divided into several wavelength ranges, it is possible to obtain information on various components of the tissue concurrently.

Additional aspects and advantages of the present invention will be set forth in part in the description which follows, and in part will be obvious from the description, or may be learned by practice of the invention.

DETAILED DESCRIPTION OF THE INVENTION

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the drawings, similar reference numerals are used for similar elements.

For an imaging catheter system that combines optical coherence tomography technology with near-infrared fluorescence imaging technology, obtaining fluorescence signals from a tissue often requires the use of an external contrast agent, which may pose difficulties in obtaining clinical approval and may increase the burden of the patient due to the possibility of the external contrast agent causing side effects. Also, since only certain molecules that the external contrast agent bonds with can be imaged, there is difficulty in concurrently imaging the various biochemical components of the tissue.

Thus, the present invention proposes an imaging catheter system that utilizes optical coherence tomography and autofluorescence lifetime imaging microscopy.

An embodiment of the invention may utilize the autofluorescence generated from the tissue, so that there is no need for an external contrast agent. An embodiment of the invention can therefore provide advantages in terms of obtaining clinical approval compared to using near-infrared imaging technology and can enable a concurrent imaging of the autofluorescence generated from various biochemical components of the tissue.

Certain embodiments of the invention are described below in more detail with reference to the accompanying drawings.

Figure 1:
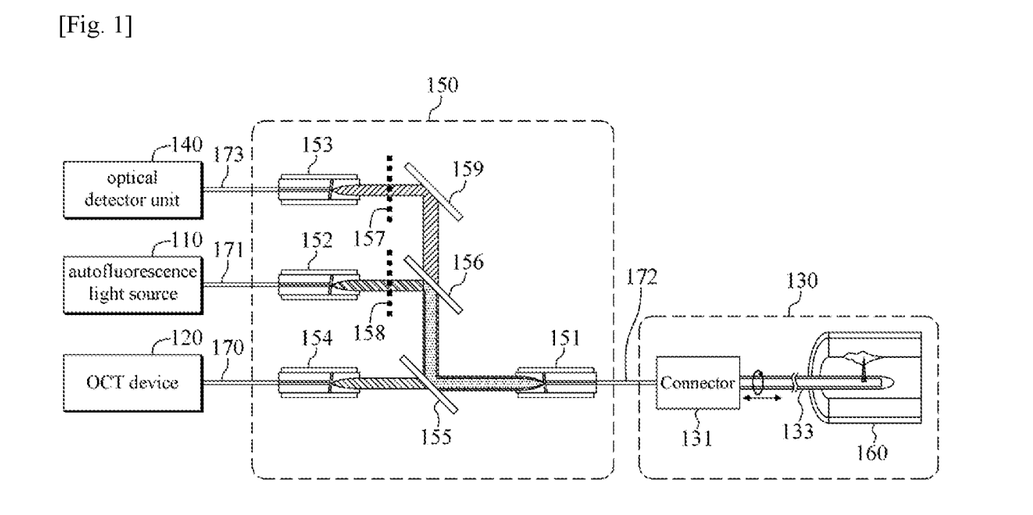
FIG. 1 illustrates an imaging catheter system according to an embodiment of the invention.
Figure 2:
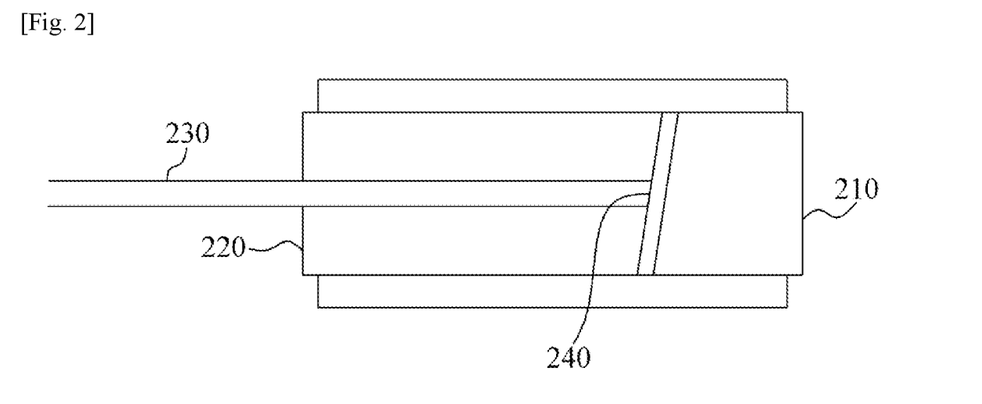
FIG. 2 illustrates a junction between a collimator and a fiber.
Figure 3A:
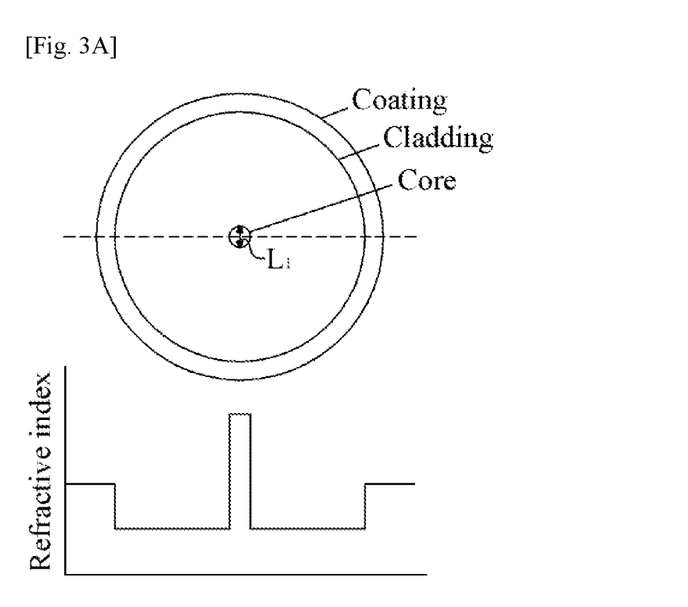
FIG. 3A and FIG. 3B illustrate the cross sections and refractive index profiles of a single-mode fiber and a double-clad fiber
Figure 3B:
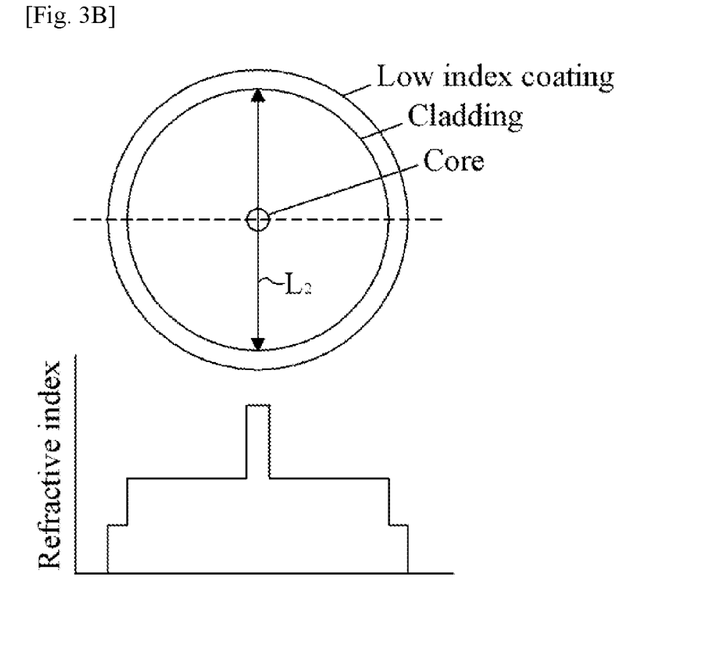

FIG. 1 illustrates an imaging catheter system according to an embodiment of the invention, FIG. 2 illustrates a collimator and a fiber joined together, and FIG. 3A and FIG. 3B illustrate the cross sections and refractive index profiles of a single-mode fiber and a double-clad fiber Referring to FIG. 1, an imaging catheter system according to an embodiment of the invention may include an autofluorescence light source 110, an OCT device 120, a catheter device 130, an optical detector unit 140, and a first optics system 150.

The autofluorescence light source 110 may output rays that allow a specimen 160 such as a blood vessel, into which a catheter 133 of the catheter device 130 is inserted, to emit autofluorescence. The wavelength of the rays outputted by the autofluorescence light source 110 may be a wavelength in the ultraviolet range and, in one example, can be a wavelength of 355 nm.

The first optics system 150 may receive input of the rays of the autofluorescence light source 110 and the rays of the OCT light source outputted from the OCT device 120, to provide these rays to the catheter device 130. Also, the first optics system 150 may transfer the autofluorescence inputted to the catheter device 130 to the optical detector unit 140 and transfer the rays of the OCT light source reflected off the specimen 160 to the OCT device 120. The wavelength of the rays of the OCT light source can be, in one example, 1250~1350 nm.

The catheter device 130 may receive input of the rays of the autofluorescence light source 110 and the rays of the OCT light source to scan the specimen 160.

The optical detector unit 140 may detect the autofluorescence generated from the specimen 160. The optical detector unit 140 can be, for example, a photomultiplier tube (PMT) detector, which is able to detect rays with very high sensitivity in ranges close to the ultraviolet, visible, and infrared rays of electromagnetic waves.

According to an embodiment of the invention, tomographic images can be generated for a specimen based on optical coherence tomography technology, and the autofluorescence generated from the components of the tissue forming the specimen can be imaged based on autofluorescence lifetime imaging microscopy technology.

Describing an imaging catheter system according to an embodiment of the invention in greater detail, the first optics system 150 may include collimators that transfer the rays of the light sources to the catheter device and dichroic mirrors 155, 156 that adjust the paths of the rays between the collimators. Certain embodiments can further include optical filters 157, 158 for increasing the signal-to-noise ratio and one or more reflection mirrors 159.

A fourth collimator 154 may receive input of the rays of the OCT light source via a single-mode fiber 170 and transfer the rays to a first dichroic mirror 155, and the first dichroic mirror 155 may allow the rays of the OCT light source to pass, transferring the rays to a first collimator 151.

A second collimator 152 may receive input of the rays of the autofluorescence light source via a multi-mode fiber or a single-mode fiber 171 and transfer the rays to the first collimator 151. Here, the rays outputted from the second collimator 152 may be reflected off the first and second dichroic mirrors 155, 156 to be transferred to the first collimator 151.

The first collimator 151 may receive input of the rays from the autofluorescence light source 110 and the rays from the OCT light source and may transfer the rays via a double-clad fiber 172 to the catheter device 130. Also, the first collimator 151 may transfer the autofluorescence generated from the specimen 160 and the rays of the OCT light source reflected off the specimen 160 to the first dichroic mirror 155.

The first dichroic mirror 155 may reflect the autofluorescence towards a second dichroic mirror 156 but pass the rays of the OCT light source towards the fourth collimator 154.

The second dichroic mirror 156 may pass the autofluorescence towards a reflection mirror 159, and the autofluorescence reflected by the reflection mirror 159 may be inputted to a third collimator 153. That is, the third collimator 153 may receive input of the autofluorescence generated from the specimen 160 via the first collimator 151 and may transfer it via the multi-mode fiber 173 to the optical detector unit 140.

The catheter device 130 may include a catheter 133 and an optics connector 131 that connects the catheter 133 with the first collimator 151. The optics connector 131 and the first collimator 151 may be connected with a double-clad fiber 172, and the catheter 133, being a consumable product, can be easily fastened and detached by way of the optics connector 131. The catheter device 130 may rotate together with the first collimator 151, and the catheter 133 can be inserted into the specimen 160 and rotated or moved back and forth to scan the inside of the specimen.

As already described above, the rays of the OCT light source may pass the first and fourth collimators 151, 154, and the setup can be designed such that the rays of the OCT light source is coupled only through the cores of the fibers joined to the first and fourth collimators 151, 154, in which case optical loss can occur when the rays of the autofluorescence light source 110 pass through the first collimator 151.

Referring to FIG. 2, which illustrates a junction between a fiber and a collimator, the transfer of rays may occur as the rays inputted via a lens in a first glass tube 210 of a collimator is focused onto the fiber 230 that is joined to a second glass tube 220. If the cladding diameter at the side where the rays are inputted, for example the fiber 172 of the first collimator 151, is greater than the core diameter at the side where the rays are transferred, for example the fiber 171 of the second collimator 152, then the lens of the first collimator 151 and the fiber 230 may be optimized to the wavelength of the autofluorescence light source 110, and reductions in coupling efficiency can be prevented even when there is no exact alignment and the focal position is slightly misplaced.

Therefore, in order to reduce the optical loss that may occur when the rays of the autofluorescence light source 110 pass through the first collimator 151, the core diameter $L_1$ of the multi-mode or single-mode fiber 171 of the second collimator 152 that receives input of the rays of the autofluorescence light source 110 can be designed to be smaller than the cladding diameter $L_2$ of the double-clad fiber 172 of the first collimator 151.

In the case described above, optical loss may also occur when the autofluorescence generated from the specimen 160 passes through the first collimator 151, and in order to reduce this optical loss, the core diameter of the multi-mode fiber 173 of the third collimator 153 can be designed to be greater than the cladding diameter of the double-clad fiber 172 of the first collimator 151.

Figure 4:
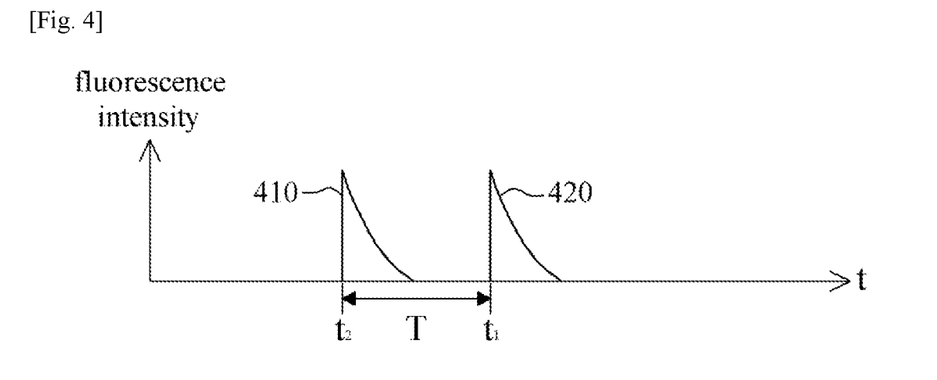
FIG. 4 illustrates a feature of an imaging catheter system according to another embodiment of the invention.

FIG. 4 illustrates a property of an imaging catheter system according to another embodiment of the invention, where the intensity of the autofluorescence generated at the core of the double-clad fiber and the intensity of the autofluorescence generated at the specimen are shown. Below, an imaging catheter system according to an embodiment of the invention is described with reference to both FIG. 1 and FIG. 3.

The cores of a double-clad fiber and a single-mode fiber can be made of germanium-doped silica to reduce attenuation within the fibers, where germanium-doped silica exhibits an autofluorescence property for wavelengths of the ultraviolet range. The autofluorescence generated thus by the cores of the double-clad fiber and single-mode fiber may act as an artifact from the perspective of the autofluorescence generated from the specimen, and therefore the effect of the artifact may have to be removed.

The autofluorescence generated in the core of the double-clad fiber 172 adjacent to the specimen 160 can be especially problematic, and as such, an embodiment of the invention can be designed such that a first time $t_1$ at which the autofluorescence generated from the specimen 160 is detected at the optical detector unit 140 is later by a threshold time or more compared to a second time $t_2$ at which the autofluorescence generated by the core of the double-clad fiber 172 in the first collimator 151 is detected at the optical detector unit 140, whereby the effects of the autofluorescence generated at the core of the double-clad fiber 172 can be minimized.

In one example, the length from one end 240 of the double-clad fiber 172 joined to the first collimator 151 up to the lens of the catheter 133 where the rays of the autofluorescence light source are outputted can be increased such that the difference between the first time and the second time is greater than or equal to the threshold time.

The intensity of fluorescence decreases with time in the form of an exponential function, as illustrated in FIG. 4, and the time passed until the intensity of the fluorescence becomes $1/e$ of the initial value $I_0$ is referred to as the fluorescence lifetime. The intensity of fluorescence decreases according to the fluorescence lifetime, and therefore, if the length of the catheter device is determined such that the autofluorescence 420 generated at the specimen is detected at the optical detector unit 140 after the intensity of the autofluorescence 410 generated by the core of the double-clad fiber 172 becomes 0, for example, as illustrated in FIG. 4, then the autofluorescence generated at the core of the double-clad fiber 172 may not act as an artifact to the autofluorescence of the specimen.

In other words, a threshold time T can be set according to the fluorescence lifetime of the autofluorescence generated by the core of the double-clad fiber 172 in the first collimator 151, and then the length from one end of the double-clad fiber 172 that is joined to the first collimator 151 up to the lens of the catheter 133 where the rays of the autofluorescence light source are outputted can be determined according to the threshold time T, in order that the autofluorescence of the specimen may be detected at the optical detector unit 140 after the threshold time T.

An imaging catheter system according to an embodiment of the invention can be utilized in a form that combines autofluorescence lifetime imaging microscopy with an imaging technology other than OCT. In such cases also, the effect of artifacts that may possibly occur from the collimators when using autofluorescence lifetime imaging microscopy can be minimized in the manner described with reference to FIG. 4.

Figure 5:
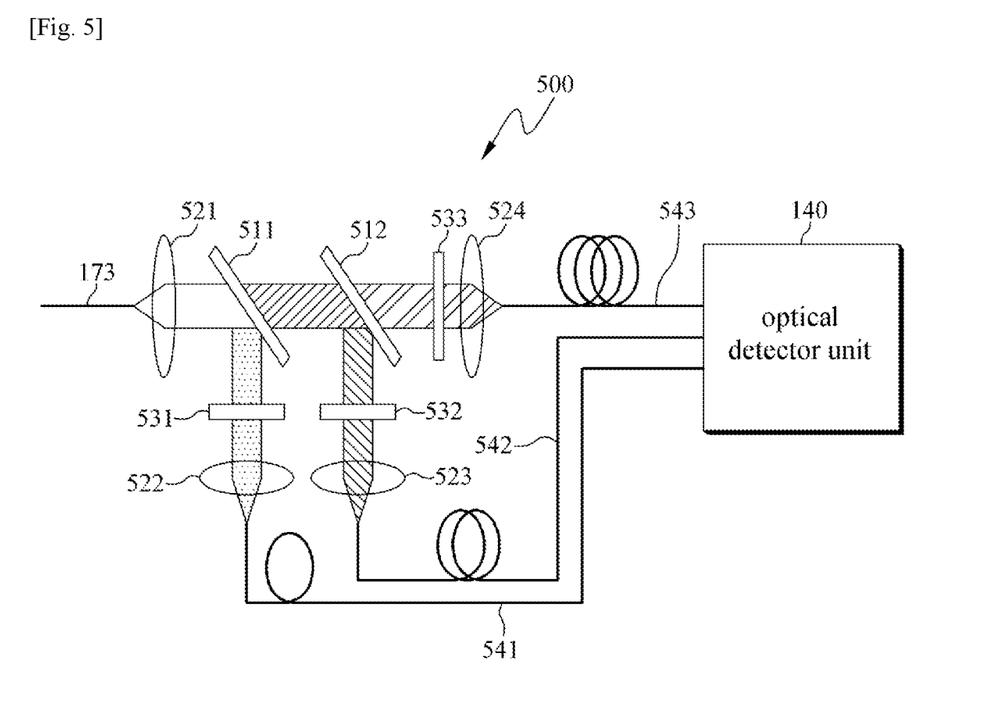
FIG. 5 illustrates a feature of an imaging catheter system according to still another embodiment of the invention.

FIG. 5 illustrates a feature of an imaging catheter system according to still another embodiment of the invention.

Referring to FIG. 5, an imaging catheter system according to an embodiment of the invention can further include a second optics system 500 that separates the rays outputted from the third collimator 153 according to wavelength. The second optics system 500 may be positioned between the optical detector unit 140 and the multi-mode fiber 173 joined to the third collimator 153 to separate the rays outputted from the third collimator 153 according to wavelength.

The rays separated according to wavelength may arrive at the optical detector unit 140 via optical fibers of different lengths, and as the rays separated according to wavelength reach the optical detector unit 140 at different times according to the lengths of the optical fibers, the optical detector unit 140 can concurrently detect the rays separated into different wavelengths.

Thus, according to an embodiment of the invention, the autofluorescence generated from the various biochemical components of a tissue can be detected with the autofluorescence divided into multiple wavelength ranges, whereby information on multiple components of the tissue can be acquired concurrently.

FIG. 5 illustrates an example in which the autofluorescence is divided into three wavelength ranges, but the number and ranges of the wavelengths to which the autofluorescence is divided can vary in different embodiments.

Describing the second optics system 500 in greater detail with reference to FIG. 5, the second optics system 500 may include multiple numbers of dichroic mirrors 511, 512, lenses 521 to 524, and filters 531 to 533. A dichroic mirror may either reflect or pass rays according to the wavelength, and a lens may form a parallel beam. A first to third optical fiber 541 to 543 can be included, which may have different lengths and may be multi-mode fibers.

A first dichroic mirror 511 may reflect rays of a first wavelength (370~410 nm) and pass rays of a second wavelength (410~500 nm) and a third wavelength (500~570 nm) from among the autofluorescence that was outputted from the multi-mode fiber 173 and passed through a first lens 521. The reflected rays may pass through a filter 531 and a lens 522 to be inputted to a first optical fiber 541.

The rays of the second wavelength may be reflected by a second dichroic mirror 512 and may pass through a filter 532 and a lens 523 to be inputted to a second optical fiber 542. The rays of the third wavelength that the second dichroic mirror 512 has allowed to pass may pass through a filter 533 and a lens 524 to be inputted to a third optical fiber 543.

The first optical fiber 541 may transfer the rays of the first wavelength to the optical detector unit 140, and the second optical fiber 542, having a different length from that of the first optical fiber 541, may transfer the rays of the second wavelength to the optical detector unit 140. The third optical fiber 543, having a different length from those of the first and second optical fibers 541, 542, may transfer the rays of the third wavelength to the optical detector unit 140.

FIG. 6 illustrates an image processing system according to an embodiment of the invention, where an imaging catheter system as described above with reference to FIG. 1 through FIG. 6 may be included.

Figure 6:
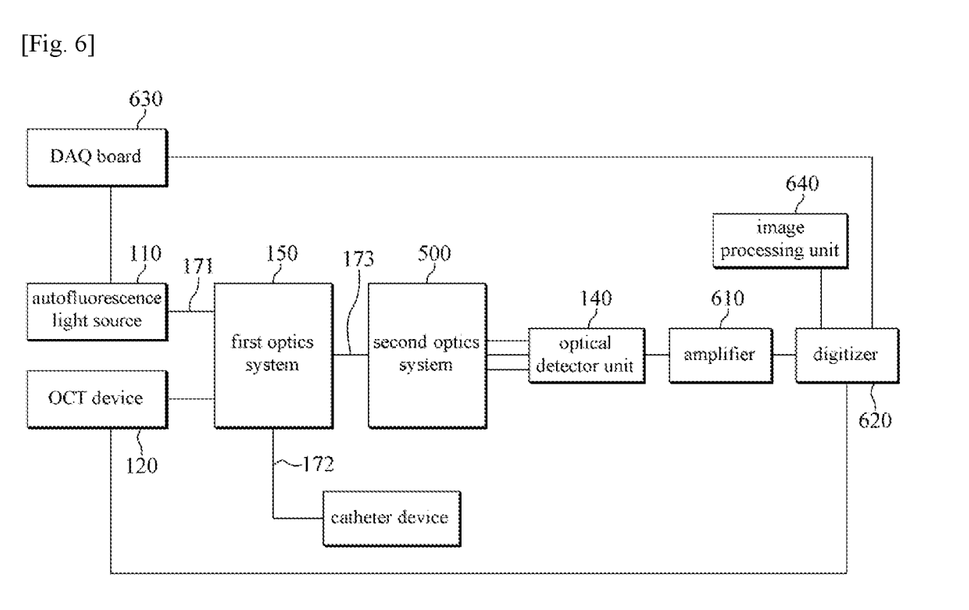
FIG. 6 illustrates an image processing system according to an embodiment of the invention.

Referring to FIG. 6, an image processing system according to an embodiment of the invention may include the imaging catheter system described above, as well as an amplifier 610, a digitizer 620, a DAQ board 630, and an image processing unit 640.

The core diameter of the multi-mode fiber 171 can be 50 um, the cladding diameter of the double-clad fiber 172 can be 105 um, and the core diameter of the multi-mode fiber 173 can be 200 um. The length from one end of the double-clad fiber 172 joined to the first collimator 151 up to the lens of the catheter through which the rays of the autofluorescence light source are outputted can be greater than or equal to 130 cm and shorter than or equal to 200 cm.

The lens used in a collimator can be a lens of a fused silica material having a transmittance of 90% or higher, so that the optical loss may be low even in a broad wavelength range (200~2200 nm).

Photons detected at the optical detector unit 140 may be converted into electrical signals and amplified at the amplifier 610, and the digitizer 620 may convert the inputted analog signals into digital signals. The image processing unit 640 may apply imaging to the digital signals.

The DAQ board 630 may control the output timing, etc., of the autofluorescence light source 110.

While the present invention is described above by way of limited embodiments and drawings that refer to particular details such as specific elements, etc., these are provided only to aid the general understanding of the present invention. The present invention is not to be limited by the embodiments above, and the person having ordinary skill in the field of art to which the present invention pertains would be able to derive numerous modifications and variations from the descriptions and drawings above. Therefore, it should be appreciated that the spirit of the present invention is not limited to the embodiments described above. Rather, the concepts set forth in the appended scope of claims as well as their equivalents and variations are encompassed within the spirit of the present invention.

What is claimed is:

1. An imaging catheter system comprising:
a pulsed autofluorescence light source;
an OCT device;
a catheter device configured to receive rays from the pulsed autofluorescence light source and an OCT light source of the OCT device and configured to scan a specimen;
an optical detector unit configured to detect autofluorescence generated from the specimen; and
a first optics system configured to transfer the autofluorescence generated from the specimen to the optical detector unit and configured to transfer a ray of the OCT light source reflected from the specimen to the OCT device,
wherein the first optics system comprises:
a first collimator configured to receive the rays from the pulsed autofluorescence light source and the OCT light source and configured to transfer the rays to the catheter device via a double-clad fiber,
wherein the autofluorescence generated from the specimen is transferred to the optical detector unit via the double-clad fiber,
wherein a first time at which the autofluorescence generated from the specimen is detected at the optical detector unit is later by a threshold time or more than a second time at which autofluorescence generated by a core of the double-clad fiber of the first collimator is detected at the optical detector unit,
wherein a length from one end of the double-clad fiber joined to the first collimator up to a lens of a catheter where the rays of the light sources are outputted is determined according to the threshold time,
wherein the threshold time is determined by a fluorescence lifetime of the autofluorescence generated by the core of the double-clad fiber of the first collimator, and
wherein the autofluorescence generated by the core of the double-clad fiber is generated before the autofluorescence generated from the specimen.

2. The imaging catheter system of claim 1, wherein the first optics system further comprises:
a second collimator configured to receive input of a ray from the pulsed autofluorescence light source and configured to transfer the ray to the first collimator via a multi-mode fiber or a single-mode fiber.

3. The imaging catheter system of claim 2, wherein a core diameter of the multi-mode fiber or the single-mode fiber of the second collimator is smaller than a cladding diameter of the double-clad fiber of the first collimator.

4. The imaging catheter system of claim 2, wherein the first optics system further comprises a third collimator configured to receive input of the autofluorescence generated from the specimen via the first collimator and transfer the autofluorescence to the optical detector unit via a multi-mode fiber, and
a core diameter of the multi-mode fiber of the third collimator is greater than a cladding diameter of the double-clad fiber of the first collimator.

5. The imaging catheter system of claim 4, comprising:
a second optics system configured to separate rays outputted from the third collimator according to wavelength;
a first optical fiber configured to transfer a ray of a first wavelength to the optical detector unit; and
a second optical fiber configured to transfer a ray of a second wavelength to the optical detector unit, the second optical fiber having a different length from a length of the first optical fiber.

6. The imaging catheter system of claim 4, wherein the first optics system further comprises:
dichroic mirrors configured to adjust paths of the rays between collimators,
optical filters configured to increase a signal-to noise ratio, and
reflection mirrors.

7. The imaging catheter system of claim 6, wherein the first optics system further comprises a fourth collimator configured to receive input of the rays of the OCT light source via a single-mode fiber and configured to transfer the rays of the OCT light source to the first collimator.

8. The imaging catheter system of claim 7, wherein the dichroic mirrors comprise:
   a first dichroic mirror configured to reflect the autofluorescence towards a second dichroic mirror and configured to pass the rays of the OCT light source towards the fourth collimator,
   a second dichroic mirror configured to pass the autofluorescence towards a reflection mirror, wherein the autofluorescence reflected by the reflection mirror is inputted to the third collimator.

9. An imaging catheter system comprising:
   a pulsed autofluorescence light source;
   a catheter device configured to receive rays inputted from the pulsed autofluorescence light source and scan a specimen;
   an optical detector unit configured to detect autofluorescence generated from the specimen; and
   a collimator configured to receive input of rays from the pulsed autofluorescence light source and transfer the rays to the catheter device via a double-clad fiber, the collimator configured to transfer the autofluorescence to the optical detector unit,
   wherein the autofluorescence generated from the specimen is transferred to the optical detector unit via the double-clad fiber,
   wherein a first time at which the autofluorescence generated from the specimen is detected at the optical detector unit is later by a threshold time or more than a second time at which autofluorescence generated by a core of the double-clad fiber of the collimator is detected at the optical detector unit,
   wherein a length from one end of the double-clad fiber joined to the collimator up to a lens of a catheter device where the rays of the pulsed autofluorescence light source are outputted is determined according to the threshold time,
   wherein the threshold time is determined by a fluorescence lifetime of the autofluorescence generated by the core of the double-clad fiber, and
   wherein the autofluorescence generated by the core of the double-clad fiber is generated before the autofluorescence generated from the specimen.

10. The imaging catheter system of claim 9, further comprising
   an OCT light source, wherein the collimator is configured to transfer rays from the OCT light source to the catheter device and transfer rays of the OCT light source reflected off the specimen to an OCT device.

11. The imaging catheter system of claim 9, further comprising:
   an optics system configured to separate rays of the autofluorescence transferred from the collimator according to wavelength;
   a first optical fiber configured to transfer a ray of a first wavelength to the optical detector unit; and
   a second optical fiber configured to transfer a ray of a second wavelength to the optical detector unit, the second optical fiber having a different length from a length of the first optical fiber.

* * * * *